United States Patent [19]

Weaver

[11] Patent Number: 5,413,095

[45] Date of Patent: May 9, 1995

[54] MOUTHPIECE WITH OXYGEN RECEIVING AND DIRECTING STRUCTURE

[75] Inventor: George W. Weaver, East Earl, Pa.

[73] Assignee: Arrow Precision Products, Inc., Reading, Pa.

[21] Appl. No.: 228,123

[22] Filed: Apr. 15, 1994

[51] Int. Cl.⁶ ........................ A61M 16/00; A62B 9/06
[52] U.S. Cl. ........................ 128/200.26; 128/207.14; 128/912; 128/DIG. 26
[58] Field of Search .............. 128/200.26, 207.14, 128/207.18, 912, DIG. 26, 207.17

[56] References Cited

U.S. PATENT DOCUMENTS

| 146,730 | 1/1974 | Vickers . | |
| D. 283,158 | 3/1986 | Jackson | D24/29 |
| 2,127,215 | 8/1938 | Gwathmey | 128/207.14 |
| 2,705,959 | 4/1955 | Elmore . | |
| 3,756,244 | 9/1973 | Kinnear et al. | 128/207.14 |
| 3,774,616 | 11/1973 | White et al. | 128/DIG. 26 |
| 3,976,080 | 8/1976 | Bormhorst et al. | 128/DIG. 26 |
| 4,231,364 | 11/1980 | Speshyock | 128/206.15 |
| 4,270,531 | 6/1981 | Blachly et al. | 128/207.14 |
| 4,425,911 | 1/1984 | Luomanen et al. | 128/DIG. 26 |
| 4,495,945 | 1/1985 | Liegner | 128/200.26 |
| 4,502,478 | 3/1985 | Lifton | 128/136 |
| 4,744,358 | 5/1988 | McGinnis | 128/DIG. 26 |
| 4,881,542 | 11/1989 | Schmidt et al. | 128/207.14 |
| 5,009,227 | 4/1991 | Nieuwstad | 128/DIG. 26 |
| 5,174,284 | 12/1992 | Jackson | 128/200.26 |
| 5,273,032 | 12/1993 | Borody | 128/207.18 |
| 5,305,742 | 4/1994 | Styers et al. | 128/DIG. 26 |

FOREIGN PATENT DOCUMENTS

| 0275105 | 7/1988 | European Pat. Off. . |
| 3543931 | 6/1987 | Germany . |
| 3719009 | 12/1988 | Germany . |
| 1558171 | 12/1979 | United Kingdom . |
| 2173105 | 10/1986 | United Kingdom . |

OTHER PUBLICATIONS

Crantock et al., *Gastrointestinal Endscopy*, vol. 92, pp. 418-420 (1992), "Supplemental low flow oxygen . . . cholangiopancratography".

OXYGYARD mouthpiece—instruction sheet.

*Primary Examiner*—Kimberly L. Asher
*Attorney, Agent, or Firm*—Amster, Rothstein & Ebenstein

[57] ABSTRACT

This invention is directed to a mouthpiece which directs oxygen into to the mouth of a patient, whether the oxygen is supplied to the patient by a single oxygen supply tube or by conventional nasal cannulae extending from a common oxygen supply tube. In addition, the mouthpiece of the invention provides auxiliary openings through which fingers can be inserted into a patient's mouth so as to allow for manual manipulation of the mouthpiece once it is placed in the mouth.

4 Claims, 3 Drawing Sheets

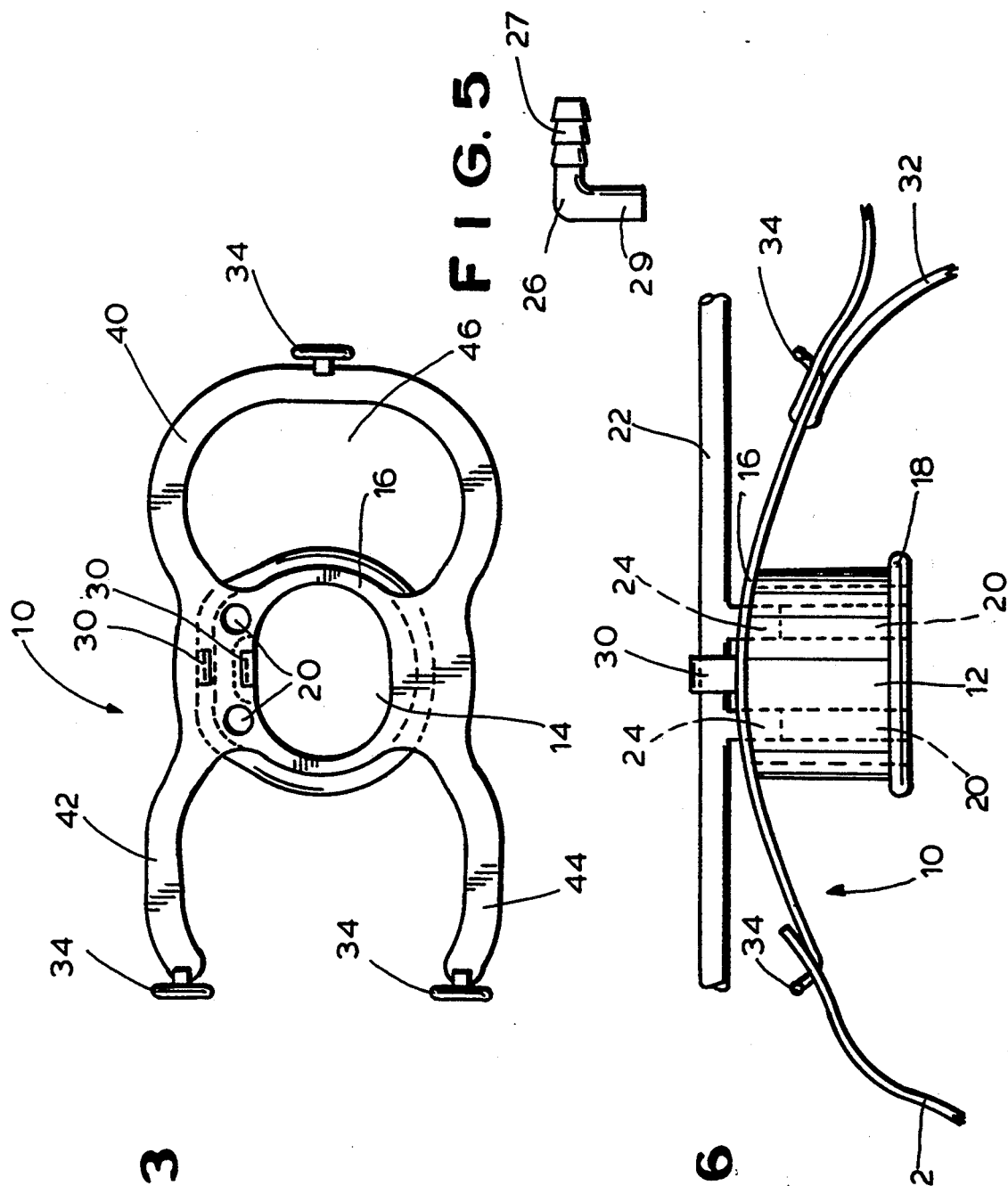

MOUTHPIECE WITH OXYGEN RECEIVING AND DIRECTING STRUCTURE

FIELD OF THE INVENTION

This invention relates to a mouthpiece for use during endoscopic procedures and, more particularly, to a mouthpiece that may be used with either a single oxygen supply tube or a pair of conventional nasal cannulae (nostril tubes which extend from a common oxygen supply tube) to direct oxygen into the mouth of a patient. Additionally, the mouthpiece of the invention provides auxiliary openings through which fingers can be inserted into the patient's mouth, thereby permitting manual manipulation of the mouthpiece once it is placed in the mouth.

BACKGROUND OF THE INVENTION

During endoscopic procedures, such as gastroscopy, it is necessary to insert medical instruments, such as tubes and scopes, into the mouth of a patient and down into the trachea. When endoscopic procedures are performed, mouthpieces are inserted into the patient's mouth to keep the mouth open and to provide an unobstructed opening therethrough. Medical instruments, such as endoscopes, are typically inserted through the opening in the mouthpiece and down into the trachea of the patient.

Several patents disclose mouthpieces for use in medical procedures. For example, U.S. Pat. No. 4,944,313 issued Jul. 31, 1990 to Katz et al. entitled "Single-Use Annular Mouthpiece" describes a mouthpiece having an annular bite body surrounded by a compressible portion. U.S. Pat. No. 5,174,284 issued Dec. 29, 1992 to Jackson entitled "Endoscopic Bite Block" describes an endoscopic bite block having a central opening as well as adjacent auxiliary openings. This mouthpiece is also shown in U.S. Pat. No. 283,158 issued Mar. 25, 1986 to Jackson entitled "Endoscopic Bite Block". U.S. Pat. No. 4,502,478 issued Mar. 5, 1985 to Lifton entitled "Medical Instrument Mouth Guard" describes a mouth guard having a central opening which extends into the mouth and a single auxiliary opening.

Although the above-described patents are directed to mouthpieces which can be used in medical procedures, including endoscopic procedures, none of the above-described patents are directed to a mouthpiece which includes structure to permit a supplemental supply of oxygen to the patient. It has been shown that if patients undergoing endoscopic and similar procedures are not provided with a supply of supplemental oxygen, oxygen desaturation occurs. See Crantock et al., *Gastrointestinal Endoscopy*, Vol. 92, pp. 418–420 (1992). When oxygen desaturation occurs, hypoxia, cardiac arrhythmia, myocardial ischemia and even death may result. Hence, it is important that a mouthpiece include structure which permits administration of supplemental oxygen to patients on whom endoscopy and similar medical procedures are performed.

A commercially available mouthpiece sold under the name OXYGUARD is formed with an integrally molded tube which extends to the side for connection to an oxygen supply tube. This integrally molded side tube (i.e. permanently attached to the mouthpiece) communicates with two channels in the mouthpiece which direct the oxygen into the nostrils of the patient and two other channels in the mouthpiece which direct oxygen into the mouth of the patient. Hence, the OXYGUARD mouthpiece diffuses the oxygen supply since it directs the oxygen to both the nostrils and the mouth, which is not preferred.

A great majority of patients upon whom endoscopy is performed breath primarily (if not solely) through the mouth during endoscopic procedures. Because the OXYGUARD mouthpiece diffuses oxygen into the nostrils as well as into the mouth, the OXYGUARD mouthpiece is not as effective in delivering oxygen to patients as is desirable. The oxygen supplied to the nostrils is wasted on a majority of patients.

More importantly, the OXYGUARD mouthpiece does not accommodate nasal cannulae which extend from a common oxygen supply tube, which are most commonly used to oxygenate patients prior to endoscopic procedures. Instead, the OXYGUARD mouthpiece can only be used with a single oxygen supply tube, which may or may not be available during endoscopic procedures. As a result, in many situations the OXYGUARD mouthpiece cannot be used. Another drawback associated with the OXYGUARD mouthpiece is that it does not have auxiliary openings which permit the insertion of fingers or auxiliary instruments into the mouth, again limiting its use in many situations.

Therefore, a need still exists to develop a versatile mouthpiece useful in endoscopic procedures, which mouthpiece delivers oxygen directly into the mouth whether the oxygen is supplied by either a pair of conventional nasal cannulae which extend from a common oxygen supply tube or a single oxygen supply tube, so as to reduce hypoxia, cardiac arrhythmia, myocardial ischemia and even death. Such a mouthpiece should also be formed with auxiliary openings so as to allow for the insertion of fingers and/or auxiliary instruments into the mouth.

It is therefore an object of this invention to provide a versatile mouthpiece which allows for the direct supply of oxygen into the mouth, whether the oxygen is supplied through a pair of conventional nostril tubes or an oxygen supply tube.

It is a further object of this invention to provide a mouthpiece which has auxiliary openings which allow for the insertion of fingers and/or instruments into the mouth.

SUMMARY OF THE INVENTION

This invention is directed to a mouthpiece having an annular bite portion to be placed within the mouth of a patient to keep the mouth open and to provide a first opening therethrough. An outer portion extends radially outwardly from one end of the annular bite portion and an inner rim extends radially outwardly from the other end of the annular bite portion. Parallel channels or passageways extend through the mouthpiece from the outer portion to the inner rim to direct oxygen into the mouth of a patient. The parallel channels are formed to receive either a pair of conventional nasal cannulae or, with the use of an adapter, a single oxygen supply tube. The mouthpiece is secured to the patient's face through use of an elastic headstrap which is secured to curved arms which extend laterally from the outer portion so as to provide auxiliary openings between the outer portion and the arms. These auxiliary openings permit the insertion of fingers and/or instruments into the patient's mouth.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 3 is a front elevational view of the mouthpiece of the invention shown without a headstrap;

FIG. 4 is a side elevational view of the mouthpiece of the invention;

FIG. 5 is a plan view of the adapter of the invention;

FIG. 6 is a bottom plan view of the mouthpiece of the invention shown receiving conventional nasal cannulae extending from a common oxygen supply tube.

DETAILED DESCRIPTION OF THE INVENTION

Figure 1:
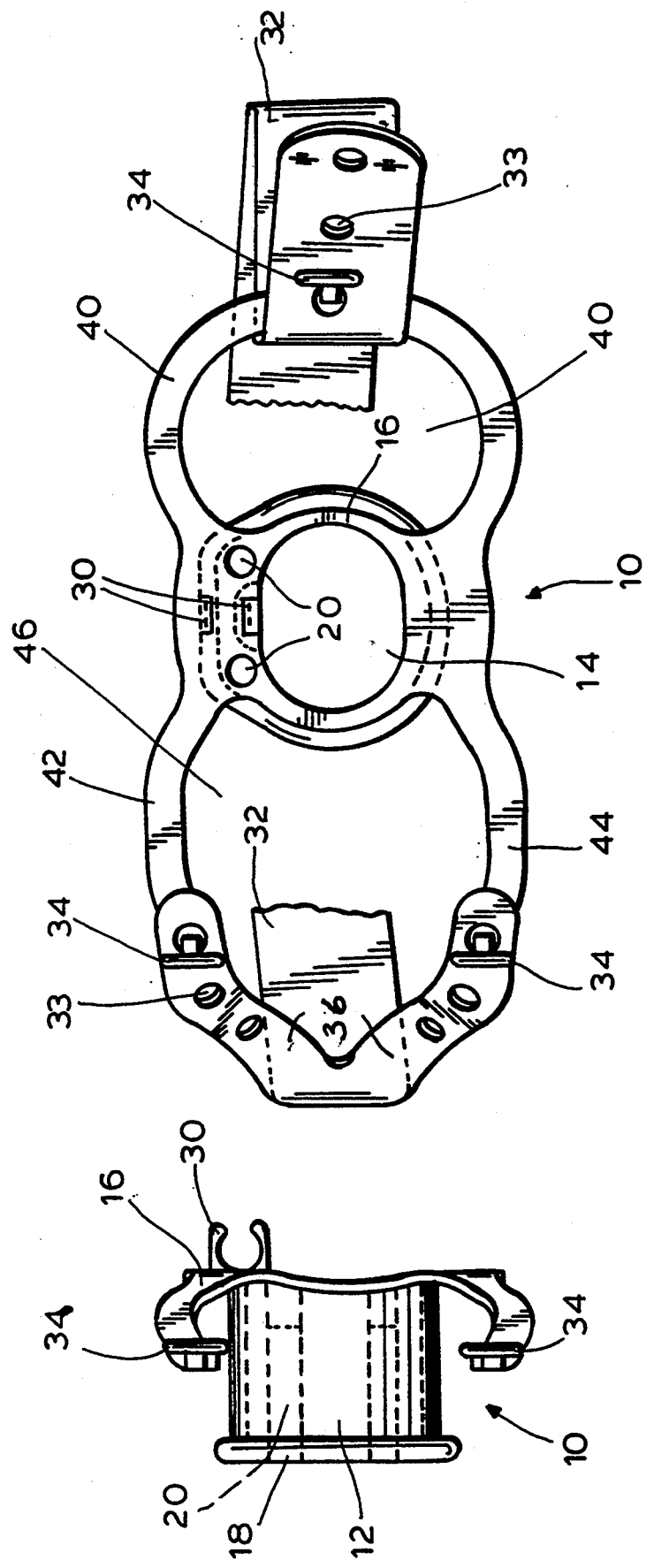
FIG. 1 is a front elevational view of a preferred embodiment of the mouthpiece of the invention.

Referring to the drawings, the reference numeral 10 generally denotes the mouthpiece of the invention. Referring to FIG. 1, mouthpiece 10 is preferably made of a flexible plastic material by injection molding, and comprises an annular bite portion 12 which forms an opening 14. The bite portion 12 is placed within a patient's mouth and serves to keep the mouth open during endoscopic procedures while the opening 14 permits medical instruments to be passed through the patient's mouth and into the trachea. The bite portion 12 may be covered on its outer surface with an annular shaped compressible pad (not shown) such that a person biting the mouthpiece will make a non-permanent impression into the compressible pad.

Figures 2, 7:
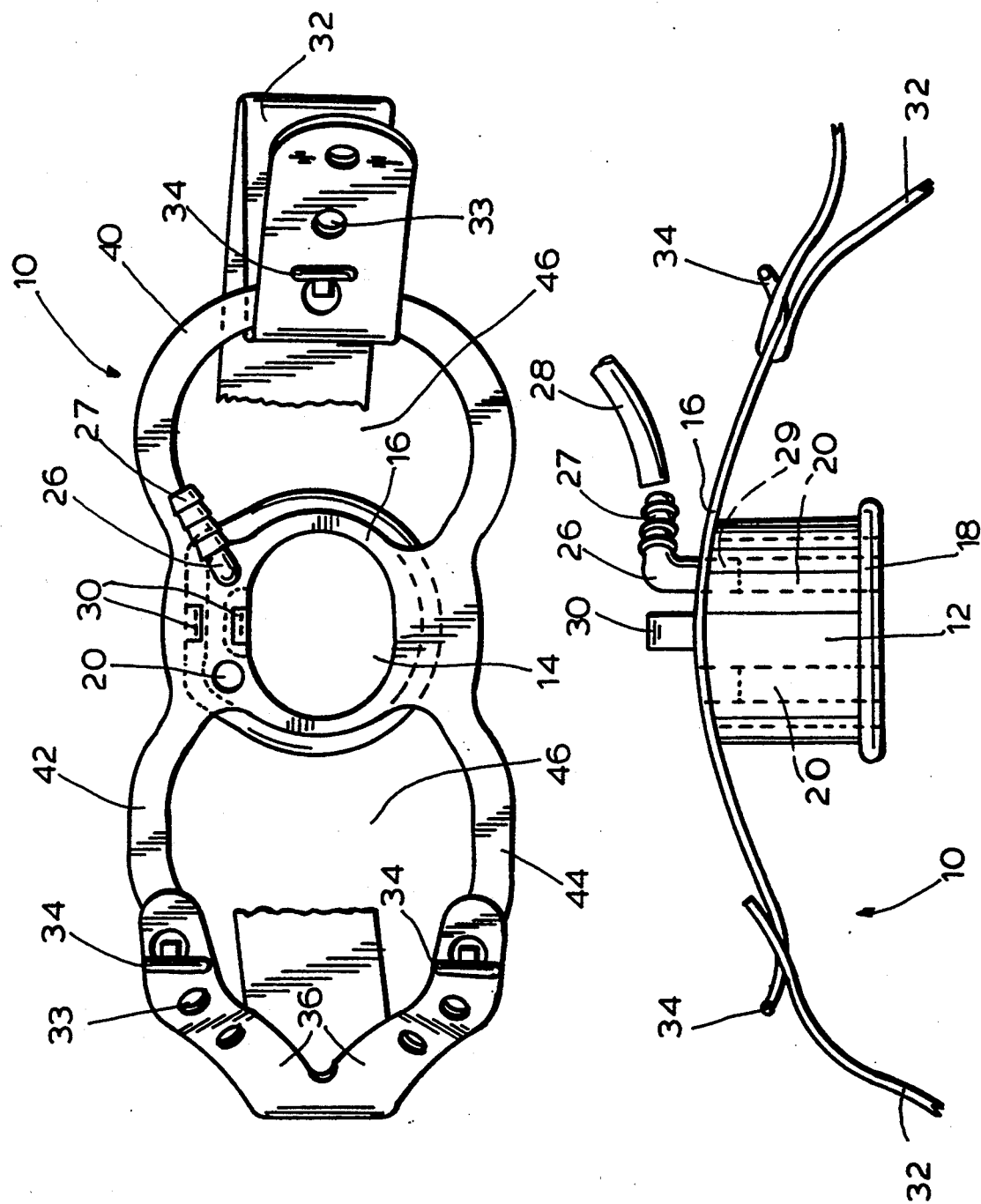
FIG. 2 is a front elevational view of the mouthpiece of the invention shown with the adapter of the invention.
FIG. 7 is a bottom plan view of the mouthpiece of the invention together with the adapter of the invention.

Referring to FIGS. 4, 6 and 7, an outer portion 16 extends radially outwardly from one end of the annular bite portion 12, so that when the mouthpiece 10 is placed in the mouth, the annular bite portion 12 is inside the mouth, and the outer portion 16 remains outside the mouth and may cover all or a portion of the lips of the patient. The outer portion 16 serves to limit movement of the annular bite portion 12 into the mouth. An inner rim 18 extends radially outwardly above the surface of the compressible pad at the other end of the annular bite portion 12 and may be grasped by the tongue, teeth or gums of the patient.

As shown in FIGS. 1, 3 and 6, the mouthpiece 10 contains two parallel channels 20 which extend from the front surface of the outer portion 16, through the annular bite portion 12 and out through the back surface of the inner rim 18. The channels 20 are formed so that a pair of conventional nasal cannulae 24 which extend from a common oxygen supply tube 22 can be inserted directly into the channels 20, as shown in FIG. 6. In this manner, oxygen supplied through the nasal cannulae 24 is directed through the channels 20 and into the patient's mouth. No oxygen is diverted into the patient's nostrils.

In order to keep the nasal cannulae 24 in the channels 20, the outer portion 16 of the mouthpiece 10 includes a tube holder made up of curved fingers 30 for securing the nasal oxygen supply tube 22 to the surface of the outer portion 16, as depicted in FIGS. 4 and 6. In this manner, the nasal cannulae 24 are retained within the channels 20. As best seen in FIGS. 4 and 6, the curved fingers 30 extend outwardly from the outer portion 16 such that a nasal oxygen supply tube 22 can be snapped between the fingers 30 and held against the surface of the outer portion 16 while the nasal cannulae 24 are located within the channels 20.

As depicted in FIGS. 2, 5 and 7, the mouthpiece 10 includes an attachable adapter 26 having a luer taper 27 at one end which luer taper can be attached to a single oxygen supply tube 28 if nasal cannulae 24 are not used. The tube 28 may be formed with a corresponding luer connector at one end for attachment to the luer taper 27 of the adapter 26 and the opposite end of the tube 28 is connected to a source of oxygen. The other end 29 of the adapter 26 is sized to be received in one of the channels 20. The end 29 of the adapter 26 may be permanently bonded into one of the channels 20, if desired. Hence, the adapter 26 is used to connect the single oxygen supply tube 28 to one of the channels 20 and, in this manner, oxygen is supplied directly into the mouth.

Referring to FIGS. 1, 2 and 3, in order to keep the mouthpiece 10 stationary in the mouth, the mouthpiece 10 is secured to the head by use of an attachable elastic headstrap 32. The headstrap 32 is formed with openings 33 at the ends thereof and at least one end is split, creating split ends 36, as shown in FIGS. 1 and 2. One end of the headstrap 32 is attached to a semi-circular arm 40 and the other end is connected to curved arms 42 and 44 all of which extend laterally from the sides of the outer portion 16 of the mouthpiece 10.

Arm 40 is semi-circular in shape and extends from the top of the outer portion 16 to the bottom of the outer portion 16. A T-shaped fastener 34 is formed at about the midpoint of the arm 40 for insertion through the headstrap openings 33, for securing one end of the headstrap 32 to the mouthpiece 10. Curved arms 42 and 44 extend from the other side of the outer portion 16, arm 42 from the top of the outer portion 16 and arm 44 from the bottom. Each of the arms 42 and 44 terminate in a T-shaped fastener 34 for insertion through the openings 33 in the split ends 36 of the headstrap 32, thereby securing the opposite ends of the headstrap 32 to the mouthpiece 10.

Arms 40, 42 and 44 are formed so as to provide auxiliary openings 46 between the outer portion 16 and the ends of the headstrap 32. This allows for the insertion of auxiliary instruments and fingers through the openings 46 and into the mouth such that the mouthpiece 10 can be manipulated. Of course, the mouthpiece can be formed with curved arms 42 and 44 on both sides of the outer portion 16, or with semi-circular arms 40 on both sides of the outer portion 16.

The mouthpiece of the invention allows for oxygen to be directed into the mouth of a patent during endoscopic procedures, whether the oxygen is supplied by either conventional nasal cannulae extending from a common oxygen supply tube or a single oxygen supply tube. Nasal cannulae which are typically used for oxygen supply may be inserted directly into the channels in the mouthpiece of the invention, thereby directing the flow of oxygen directly into the mouth. Alternatively, the adapter can be used to connect a single oxygen supply tube to a channel so as to direct the flow of oxygen directly into the mouth. The supply of oxygen directly into the mouth results in reduction of hypoxia, cardiac arrhythmia, myocardial ischemia and even death.

In addition, the auxiliary openings in the mouthpiece of the invention provide clearance for fingers, thereby allowing for manual manipulation of the mouthpiece once it is placed in the mouth. Because the mouthpiece of the invention can be manipulated, it can be moved in such a manner to increase patient comfort level. These openings also allow for the insertion of auxiliary instruments into the mouth. In addition, the mouthpiece of the invention can be made of a flexible material, such as plastic, which also increases patient comfort level. Finally, the mouthpiece of the invention can be disposable.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

I claim:

1. A mouthpiece comprising:
   (a) an annular bite portion for placement within the mouth of a patient so as to keep the mouth of the patient open and provide an opening into the mouth of the patient;
   (b) an outer portion extending radially outwardly at one end of said annular bite portion for placement outside the mouth of the patient;
   (c) two parallel channels formed in said mouthpiece and extending through said outer portion and said annular bite portion and exiting exclusively into the mouth of the patient, said channels being formed to receive one of (i) a pair of nasal cannulae which extend from a common oxygen supply tube and (ii) a single adapter extending from an oxygen supply tube, so that all of the oxygen from said oxygen supply tube is supplied directly and exclusively into the mouth of the patient;
   (d) a tube holder for securing said oxygen supply tube to said mouthpiece and retaining the nasal cannulae in said channels; and
   (e) a headstrap attachable to said mouthpiece to secure said annular bite portion of said mouthpiece within the mouth of the patient.

2. The mouthpiece of claim 1 wherein said mouthpiece further includes arms extending laterally from said outer portion so as to create auxiliary openings between said outer portion and said arms such that fingers or instruments can be inserted through said auxiliary openings and into the mouth of the patient.

3. The mouthpiece of claim 2 wherein said arms include fasteners for attaching said headstrap to said arms.

4. The mouthpiece of claim 1 wherein said tube holder comprises curved fingers extending outwardly from said outer portion such that an oxygen supply tube can be snapped between said curved fingers and held against the outer portion, thereby retaining the nasal cannulae in said channels.

* * * * *